(12) United States Patent
    Asleson et al.

(10) Patent No.: US 10,391,305 B2
(45) Date of Patent: *Aug. 27, 2019

(54) TELESCOPING CATHETER DELIVERY SYSTEM FOR LEFT HEART ENDOCARDIAL DEVICE PLACEMENT

(71) Applicant: Medtronic, Inc., Minneapolis, MN (US)

(72) Inventors: Andrea J Asleson, Maple Grove, MN (US); Zhongping Yang, Woodbury, MN (US); Michael W Kimmel, Edina, MN (US); Kyle R Marquard, Lino Lakes, MN (US); Laurie D Foerster, Mound, MN (US)

(73) Assignee: Medtronic, Inc., Minneapolis, MN (US)

( * ) Notice: Subject to any disclaimer, the term of this patent is extended or adjusted under 35 U.S.C. 154(b) by 96 days.

This patent is subject to a terminal disclaimer.

(21) Appl. No.: 15/487,290

(22) Filed: Apr. 13, 2017

(65) Prior Publication Data
    US 2017/0216575 A1    Aug. 3, 2017

Related U.S. Application Data

(60) Continuation of application No. 14/791,995, filed on Jul. 6, 2015, now abandoned, which is a division of
    (Continued)

(51) Int. Cl.
    *A61N 1/05*    (2006.01)
    *A61B 17/00*    (2006.01)
    (Continued)

(52) U.S. Cl.
    CPC ........ *A61N 1/056* (2013.01); *A61B 17/00234* (2013.01); *A61B 17/3468* (2013.01);
    (Continued)

(58) Field of Classification Search
    None
    See application file for complete search history.

(56) References Cited

U.S. PATENT DOCUMENTS

| 5,497,774 A | 3/1996 | Swartz |
| 5,755,760 A | 5/1998 | Maguire |

(Continued)

FOREIGN PATENT DOCUMENTS

WO    WO 2008/031103 A2    3/2008

OTHER PUBLICATIONS

Berry M. van Gelder, PhD, et al. Transseptal endocardial left ventricular pacing: An alternative technique for coronary sinus lead placement in cardiac resynchronization therapy. Heart Rhythm, vol. 4, No. 4, Apr. 2007,454-460.

(Continued)

*Primary Examiner* — Erica S Lee (57) ABSTRACT

A transseptal catheter delivery system includes an elongate first tubular member and an elongate second tubular member receivable within the first tubular member. The first tubular member includes an adjustable portion adjacent a distal end. The second tubular member is adapted to receive an instrument to be placed in the left ventricle, and includes a curved portion adjacent its distal end in a relaxed state. The adjustable portion is deflectable toward the atrial septum to guide a puncturing tool and/or guide insertion of the second tubular member through a septal puncture into the left atrium. Within the left atrium, the curved portion is oriented toward the left ventricle to guide insertion of a guide wire, and subsequently the second tubular member, into the left ventricle. Methods of transvenously accessing a left ventricle are also provided.

17 Claims, 9 Drawing Sheets

Related U.S. Application Data application No. 12/916,345, filed on Oct. 29, 2010, now Pat. No. 9,072,872.

(51) Int. Cl.
*A61B 17/34* (2006.01)
*A61M 25/01* (2006.01)
*A61M 25/06* (2006.01)
*A61M 29/00* (2006.01)
*A61F 2/24* (2006.01)
*A61B 18/14* (2006.01)
*A61M 25/09* (2006.01)
A61M 25/00 (2006.01)
A61B 18/00 (2006.01)

(52) U.S. Cl.
CPC ........ *A61B 18/1492* (2013.01); *A61F 2/2427* (2013.01); *A61M 25/0133* (2013.01); *A61M 25/0662* (2013.01); *A61M 25/09* (2013.01); *A61M 29/00* (2013.01); *A61B 2017/00247* (2013.01); *A61B 2017/00331* (2013.01); *A61B 2018/00351* (2013.01); *A61B 2018/00601* (2013.01); *A61B 2018/144* (2013.01); *A61M 25/0041* (2013.01); *A61M 2025/0175* (2013.01); *A61M 2025/0681* (2013.01); *A61M 2210/125* (2013.01)

(56) References Cited

U.S. PATENT DOCUMENTS

| | | | |
|---|---|---|---|
| 5,807,318 A | 9/1998 | St. Goar et al. | |
| 6,090,084 A | 7/2000 | Hassett | |
| 6,156,018 A | 12/2000 | Hassett | |
| 6,526,302 B2 | 2/2003 | Hassett | |
| 6,579,279 B1 | 6/2003 | Rabiner | |
| 6,650,923 B1 | 11/2003 | Lesh | |
| 6,755,790 B2 | 6/2004 | Stewart | |
| 6,994,094 B2 | 2/2006 | Schwartz | |
| 7,020,518 B2 | 3/2006 | Zheng | |
| 7,056,294 B2 | 6/2006 | Khairkhahan | |
| 7,079,895 B2 | 7/2006 | Verbeek | |
| 7,122,034 B2 | 10/2006 | Belhe | |
| 7,248,913 B2 | 7/2007 | Hassett | |
| 7,321,798 B2 | 1/2008 | Muhlenberg | |
| 7,450,999 B1 | 11/2008 | Karicherla | |
| 7,678,081 B2 | 3/2010 | Whiting | |
| 7,717,899 B2 | 5/2010 | Bowe | |
| 7,983,765 B1 | 7/2011 | Doan et al. | |
| 8,401,673 B2 | 3/2013 | Bowe et al. | |
| 8,753,312 B2 | 6/2014 | Bowe et al. | |
| 9,072,872 B2 | 7/2015 | Asleson et al. | |
| 2001/0044591 A1 | 11/2001 | Stevens et al. | |
| 2003/0144657 A1 | 7/2003 | Bowe | |
| 2004/0133113 A1 | 7/2004 | Krishnan | |
| 2004/0230283 A1 | 11/2004 | Prinzen | |
| 2005/0101984 A1 | 5/2005 | Chanduszko | |
| 2005/0137669 A1 | 6/2005 | Krishnan | |
| 2006/0009737 A1 | 1/2006 | Whiting et al. | |
| 2006/0276710 A1 | 12/2006 | Krishnan | |
| 2007/0021739 A1 | 1/2007 | Weber | |
| 2007/0083168 A1 | 4/2007 | Whiting | |
| 2007/0088355 A9 | 4/2007 | Auth | |
| 2007/0270741 A1 | 11/2007 | Hassett | |
| 2008/0208166 A1 | 8/2008 | Goode | |
| 2009/0125078 A1 | 5/2009 | Kaiser | |
| 2009/0326630 A1 | 12/2009 | Tobin | |
| 2010/0042110 A1 | 2/2010 | Kelley | |

OTHER PUBLICATIONS

David D. Spragg, MD, et al. Optimal Left Ventricular Endocardial Pacing Sites for Cardiac Resynchronization Therapy in Patients With Ischemic Cardiomyopathy. Journal of the American College of Cardiology, vol. 56, No. 10, Aug. 31, 2010, 774-781.

Frank A. Bracke, et al. Left ventricular endocardial pacing improves the clinical efficacy in a non-responder to cardiac resynchronization therapy: role of acute haemodynamic testing. European Society of Cardiology. Europace Advance Access published Mar. 2, 2010, 3 pages.

Nicolas Derval, MD, et al. Optimizing Hemodynamics in Heart Failure Patients by Systematic Screening of Left Ventricular Pacing Sites. Journal of the American College of Cardiology, vol. 55, No. 6, Feb. 9, 2010, 566-575.

Judkins rightcoronary catheter. Cardiophile MD, http://cardiophile.org/2009/02/judkins-right-coronary-catheter.html, printed Oct. 21, 2010, 2 pages.

Medtronic Fully Integrated CRT Implant, http://www.medtronic.com/for-healthcare-professionals/products-therapies/cardiac-rhythm/cardiac-resynchronization-therapy-devices/fully-integrated-crt-implant-system/delivery-systems/index.htm, printed Oct. 18, 2010, 5 pages.

Medtronic ATTAIN® 6227DEF Technical manual, 2006, 11 pages.

Medtronic ATTAIN SELECT® II6248DEL Technical manual, 2006, 15 pages.

Medtronic SELECTSITE® C304-S59/C304-L69/C304-XL74 Technical manual, 2006, 7 pages.

Medtronic ATTAIN COMMAND™ 6250C, 6250S Technical manual, 2008, 7 pages.

(PCT/US2011/058375) PCT Notification of Transmittal of the International Search Report and the Written Opinion of the International Searching Authority.

TELESCOPING CATHETER DELIVERY SYSTEM FOR LEFT HEART ENDOCARDIAL DEVICE PLACEMENT

RELATED APPLICATION

This application is a continuation of U.S. patent application Ser. No. 14/791,995 filed Jul. 6, 2015 entitled "TELESCOPING CATHETER DELIVERY SYSTEM FOR LEFT HEART ENDOCARDIAL DEVICE PLACEMENT", which is a divisional of U.S. patent application Ser. No. 12/916,345, filed Oct. 29, 2010 entitled "TELESCOPING CATHETER DELIVERY SYSTEM FOR LEFT HEART ENDOCARDIAL DEVICE PLACEMENT", now U.S. Pat. No. 9,072,872, herein incorporated by reference in its entirety.

FIELD

Embodiments of the present invention generally relate to systems for delivering medical devices to the heart, and more particularly relate to catheter based delivery systems for left heart device placement.

BACKGROUND

In some cases it can be desirable to deliver and position a medical device in or near the left side of a patient's heart for diagnosing and/or treating cardiovascular disease. As just one example, patients with heart failure can in some cases be treated with cardiac resynchronization therapy (CRT) delivered with a collection of electrical leads, one of which is placed proximate the left ventricle for bi-ventricular pacing. A traditional placement for a left ventricular (LV) lead is a transvenous placement into one of the tributaries of the coronary sinus (CS). By some estimates, however, up to 40-50% of CRT patients do not respond to CRT with a traditional CS lead placement. One alternative to a traditional CS lead placement is a left ventricular endocardial lead placement. An LV endocardial placement may be useful for patients with poor CS lead access or stability or those with failed CS implants. Accordingly, there is a growing interest in LV endocardial lead placement.

Delivery catheters are often used to position electrical leads (and other medical devices) at various cardiovascular sites (e.g., such as a LV endocardial placement) within a patient via minimally invasive techniques. These catheters are constructed having a lumen, which provides a pathway to the implant site, through which an implanting physician may pass the medical device without encountering anatomical obstructions. Some delivery catheters include mechanisms, such as pull-wire actuation, which allow the implanting physician to actively change a curvature of the catheter in order to direct a distal tip of the catheter to a target implant site. Such catheters may be referred to as being "steerable" or "deflectable." Other delivery catheters have resilient, pre-formed curvatures tailored to position a distal tip thereof at a particular anatomical site from a particular percutaneous access site. Such "fixed-shape" catheters can thus eliminate or reduce the need to actively control the curvature during the implant procedure.

In some cases delivery systems may include combinations of two or more steerable and/or fixed shape catheters. U.S. Patent Application Publication 2003/0144657 discloses one example of a catheter assembly employing an outer catheter with a pre-formed distal end and an inner catheter with a pre-formed distal end. Relative rotation and extension of the inner and outer catheters provides adjustable shaping of the catheter assembly's distal tip for improved locating and cannulating of, e.g., the coronary sinus via the right atrium. Another example of a coronary sinus access system is the ATTAIN SELECT® II 6248DEL delivery catheter system available from Medtronic, Inc., which can be used with an outer catheter such as the ATTAIN® 6227DEF deflectable catheter delivery system, also available from Medtronic, Inc.

Another common approach for accessing the left side of the heart is a transseptal access from the right atrium through the intra-atrial septum to the left atrium. U.S. Pat. No. 7,678,081, and U.S. Patent Application Publication 2007/0083168 provide examples of catheter systems employing a right to left atrial transseptal approach. U.S. Pat. No. 7,678,081 discloses, among other things, a catheter system including a guiding catheter, an access catheter, and a guide wire, which may be introduced to the right atrium from an inferior or a superior route. The catheter system includes a tissue penetration member carried by the access catheter for penetrating the septal wall. U.S. Patent Application Publication 2007/0083168 discloses another catheter system that accesses the left atrium from the right atrium by penetrating the intra-atrial septal wall. Among other things, the publication discloses a system including a stabilizer sheath having a side port, a shaped guiding catheter configured to exit the side port, and a tissue penetration member disposed within the guide catheter.

Methods of transvenously accessing the left ventricle are also known in the art. For example, a left heart catheterization can provide access to the left ventricle in a retrograde direction across the aortic valve, or a transseptal cardiac catheterization can access the left ventricle from the right atrium through the intra-atrial septum and left atrium. U.S. Pat. No. 6,156,018 discloses at least one example of the latter approach using a right femoral vein/inferior vena cava access. Another transseptal approach to the left ventricle includes the use of a Medtronic ATTAIN® 6227DEF deflectable catheter delivery system with a right Judkins catheter. Berry M. van Gelder, PhD, et al. Transseptal endocardial left ventricular pacing: An alternative technique for coronary sinus lead placement in cardiac resynchronization therapy. Heart Rhythm, Vol 4, No 4, April 2007, 454-460.

While a large number of catheter systems and delivery methods are presently available for accessing the heart, there remains a need for improved systems, especially for accessing the left ventricle of the heart.

SUMMARY

Embodiments of the invention generally provide transseptal delivery systems and methods for accessing a left ventricle of a heart. According to one aspect of the invention, a transseptal delivery system for a heart includes an elongate first tubular member and an elongate second tubular member. The first tubular member defines a first lumen extending between a proximal end and a distal end of the first tubular member, and has an adjustable portion adjacent its distal end. The second tubular member is receivable within the first tubular member and defines a lumen extending between a proximal end and a distal end of the second tubular member. The lumen of the second tubular member is adapted to receive a puncturing tool and an instrument to be placed in the heart. The second tubular member also has a curved portion adjacent its distal end in a relaxed state.

When deployed with the first tubular member extending through a superior entry point into a right atrium of the heart, the adjustable portion of the first tubular member is deflectable toward an atrial septum of the heart thereby providing an outlet at its distal end to i) guide the puncturing tool toward the atrial septum for creating a septal puncture, and ii) guide insertion of the second tubular member through the septal puncture into a left atrium of the heart. After extending the second tubular member through the septal puncture into the left atrium while maintaining the first tubular member in the right atrium, the curved portion of the second tubular member is oriented toward a left ventricle of the heart. An outlet at its distal end can thus guide insertion of a guide extending through the first and the second tubular members into the left ventricle. Thereafter, the outlet of the first tubular member, while remaining in the right atrium, supports advancement of the second tubular member along the guide into the left ventricle. With the first tubular member remaining in the right atrium and the second tubular member extending into the left ventricle, the lumen of the second tubular member provides a passage for advancing the instrument into the left ventricle.

According to another aspect of the invention, a transseptal delivery system for a heart includes an elongate first tubular member defining a first lumen extending between a proximal end and a distal end of the first tubular member. The system also includes an elongate second tubular member receivable within the first tubular member. The second tubular member defines a lumen extending between a proximal end and a distal end of the second tubular member adapted to receive a lead. The first tubular member includes an adjustable portion adjacent its distal end and the second tubular member includes a curved portion adjacent its distal end. When the first tubular member is extending into a right atrium of the heart, the adjustable portion of the first tubular member is deflectable toward an atrial septum of the heart thereby providing an outlet at its distal end to guide insertion of the second tubular member through a septal puncture into a left atrium of the heart. Thereafter, with the first tubular member remaining in the right atrium and the second tubular member extending through the septal puncture into the left atrium, the curved portion of the second tubular member is directed toward a left ventricle of the heart. The second tubular member includes an outlet at its distal end that guides insertion of a guide extending through the first and the second tubular members into the left ventricle. With the first tubular member remaining in the right atrium, the outlet of the first tubular member supports advancement of the second tubular member along the guide into the left ventricle. The second tubular member is rotatable within the first tubular member and the lumen of the second tubular member provides a rotatable passage for placement of the lead at a plurality of sites on an endocardial wall of the left ventricle.

According to another aspect of the invention, a transseptal delivery system includes a lead delivery catheter that is telescopically received within a deflectable catheter. The deflectable catheter includes a deflectable portion adjacent its distal end that is adapted to approach the intra-atrial septum of a heart when advanced through the superior vena cava into the right atrium of the heart. The lead delivery catheter includes a resilient curved portion adjacent its distal end that is adapted to direct the delivery system into the left ventricle after having been advanced through the atrial septum into the left atrium.

According to another aspect of the invention, a transseptal delivery system or kit includes a deflectable catheter, a lead delivery catheter, a dilator, and a septal puncturing tool and/or a guide wire. When assembled and initially deployed, the components are coaxially positioned in order from the innermost member: guide wire and/or septal puncturing tool, dilator, lead delivery catheter, and deflectable catheter. After accessing the left ventricle and withdrawing the guide wire/puncturing tool and dilator, the coaxial deflectable catheter and lead delivery catheter provide a lead delivery passage from the patient exterior to the atrial septum and the lead delivery catheter alone provides a lead delivery passage from the atrial septum to the left ventricle.

According to another aspect of the invention, a method for transseptal delivery in a heart is provided. The method includes advancing an elongate first tubular member through a superior vena cava into a right atrium of the heart. The first tubular member defines a first lumen extending between a proximal end and a distal end of the first tubular member. The first tubular member also has an adjustable portion adjacent its distal end. The method further includes deflecting the adjustable portion of the first tubular member within the right atrium toward an atrial septum of the heart and advancing a stiffening member through the first tubular member and through a septal puncture in the atrial septum into a left atrium of the heart. The method also includes advancing an elongate second tubular member through the first tubular member and through the septal puncture into the left atrium over the stiffening member while maintaining the first tubular member within the right atrium. The second tubular member defines a lumen extending between a proximal end and a distal end of the second tubular member. The lumen receives the stiffening member. The second tubular member has a normally curved portion adjacent its distal end that straightens when advanced through the first tubular member and over the stiffening member. The method further includes withdrawing the stiffening member from at least a portion of the second tubular member, thereby allowing the curved portion of the second tubular member to regain its normally curved shape, thereby directing an outlet at the distal end of the second tubular member toward a left ventricle of the heart. The method also includes advancing a guide through the second tubular member into the left ventricle, advancing the second tubular member over the guide into the left ventricle while maintaining the first tubular member within the right atrium, and advancing an instrument through the second tubular member into the left ventricle.

Embodiments of the present invention can optionally provide one or more of the following features and/or advantages. In some cases the second tubular member is rotatable within the first tubular member to facilitate lead placement at a variety of locations within the left ventricle. The second tubular member is rotatable through an angular range of motion, which in some cases is at least about 360 degrees. A system or kit at a minimum preferably, though not necessarily, provides the first and the second tubular members. In some cases, though, a system or kit may optionally also include a dilator receivable within the second tubular member for facilitating advancement of the second tubular member through the septal puncture. The system/kit may also optionally include a puncturing tool, such as an RF wire or a transseptal needle that can be advanced through the second tubular member for puncturing the septal wall. In some cases the system/kit may also include other components.

While it is contemplated that embodiments will be useful for placing electrical leads within the left ventricle, a number of other advantageous uses are available with exemplary catheter systems. For example, exemplary systems may be used for delivering other therapies to the left side of the heart, including leaded or leadless sensors, leadless pacers, and other items.

In addition, some exemplary catheter systems advantageously provide a single, integrated system for transvenously accessing the left heart from a superior access point. For example, a surgeon can insert the entire delivery system into a patient's vasculature from a superior location, such as the left or right subclavian vein. In one embodiment an RF transseptal wire also acts as a guide wire and is inserted through the patient's vasculature into the right atrium. A deflectable catheter can then be tracked over the guide wire into the right atrium and deflected back toward the atrial septum to align the transseptal guide wire with a preferred puncture point in the atrial septum (e.g., the fossa ovalis). After puncturing the atrial septum, the guide wire, a dilator, and a lead delivery catheter can be tracked into the left atrium, redirected toward the mitral valve, and advanced into the left ventricle, thus providing a lead delivery passage upon withdrawing the dilator and guide wire. Accordingly, some embodiments of the invention can avoid the use of multiple access points and multiple transvenous passages, thus limiting trauma and speeding recovery time for the patient.

These and various other features and advantages will be apparent from a reading of the following detailed description.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION OF THE PREFERRED EMBODIMENTS

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
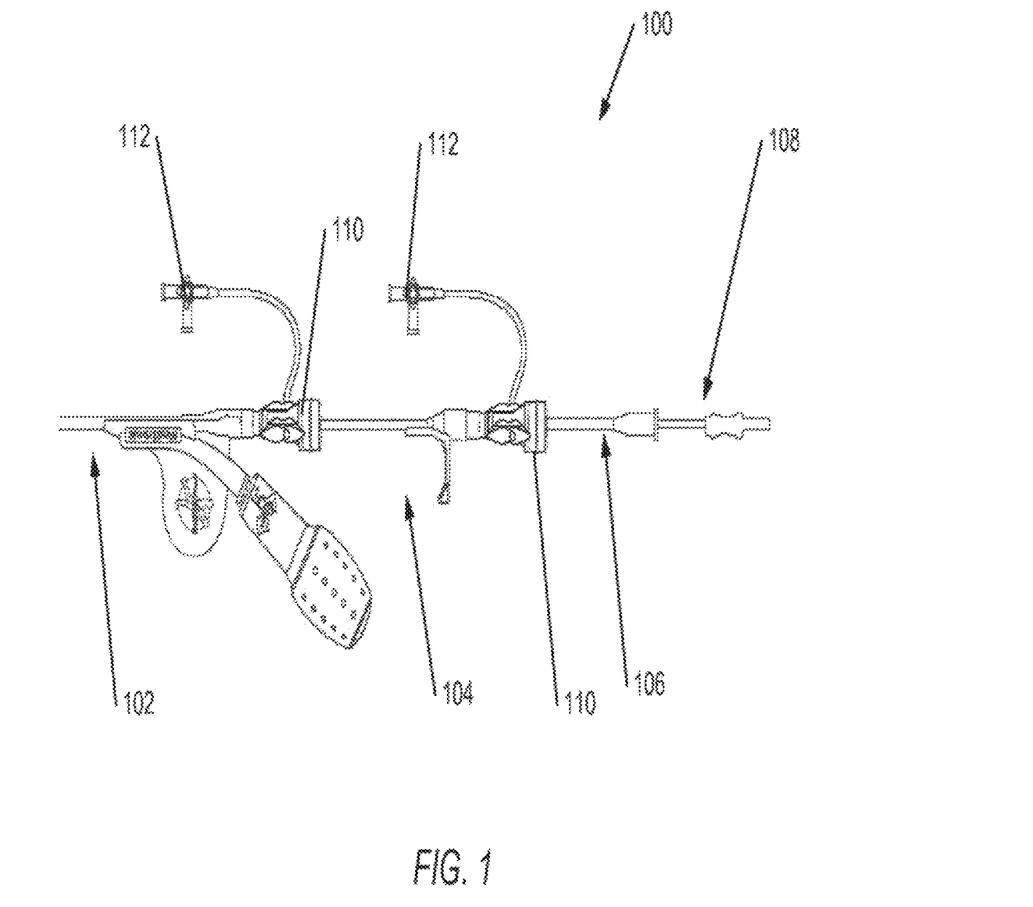
FIG. 1 is a partial side view of a catheter delivery system in accordance with an embodiment of the invention.

FIG. 1 is a partial perspective view of a catheter delivery system 100 in accordance with an embodiment of the invention. Among other things, the delivery system 100 includes an outer deflectable catheter 102, an inner delivery catheter 104, a dilator 106, and a transseptal puncturing tool 108 in the from of a radio frequency (RF) transseptal wire. Each of the outer deflectable catheter 102, inner delivery catheter 104 and dilator 106 includes an inner lumen, and as shown in FIG. 1, the components are received together in a telescoping fashion with the puncturing tool 108 at the center of the nested components. The delivery system 100 thus provides a multi-functional system that integrates a steerable, configurable delivery catheter system with transseptal puncturing capability. Accordingly, the delivery system 100 provides a one-stop solution for steering through vasculature to a septal wall, puncturing the wall, and delivering a payload through the septal puncture, all from a single entry point.

Returning to FIG. 1, the delivery system 100 also includes valves 110 and associated side ports 112 positioned between the components for limiting blood outflow while also providing access to the inner lumens of the components. Also, although not shown in FIG. 1, the catheter delivery system 100 may optionally be provided with a percutaneous needle and a syringe for inserting the delivery system 100 into a patient. The system may also include a catheter slitter, a guide wire tip straightener, and/or any other desirable components known in the art. In some cases a typical guide wire may be used in place of or in addition to the RF wire 108 to advance the delivery system 100 through the patient's vasculature. As just one example, the delivery system 100 may be routed through a preexisting septal puncture e.g., made by another device or naturally occurring (e.g., patent foramen ovale).

The transseptal puncturing tool 108 can be provided in any suitable form, and in some cases may comprise a transvenous needle for mechanical puncturing or an RF wire as illustrated. For example, in one embodiment the puncturing tool 108 is an RF Transseptal Wire available from Baylis Medical. Preferably, the RF transseptal wire (or optionally standard guide wire) includes a small curve or "pig tail" on its distal end to avoid unwanted perforation of other structures once through the septum when coming from a superior approach. Similarly, the dilator 106 can be provided in a number of formats and in one case is a Baylis Medical Transseptal Dilator. Preferably the dilator 106 provides a continuous, smooth transition between the puncturing tool/guide wire and the delivery catheter 104 in order to avoid undesired tearing or other tissue damage as the larger diameter delivery catheter 104 is advanced through the septal puncture.

In some cases two or more components of the delivery system 100 may be packaged and sold together as a kit. For example, one kit can include all of the components just described above. In some embodiments, a delivery system and/or kit at a minimum includes the deflectable catheter 102 and the delivery catheter 104 as they provide complementary functionality that when combined provides a more flexible and configurable delivery system. For example, in some cases the delivery and deflectable catheters are adapted to cooperatively provide a delivery passage to the left ventricle of a human's heart. In some embodiments the deflectable and delivery catheters 102, 104 are advantageously adapted to access the left heart from a superior access point (e.g., a subclavian access point) and a trans-septal approach across the intra-atrial septum. In some cases curves on the lead delivery catheter 104 are designed to help direct the system 100 through the mitral valve and also create sufficient access to multiple sites on the left ventricular endocardium. The delivery system 100 is thus extremely useful for delivering medical instruments such as leads, leaded or leadless sensors and/or pacers, catheters, guide wires, and other instruments to the left heart while minimizing patient trauma normally associated with multiple entry points and multiple transvenous pathways.

Figure 2A:
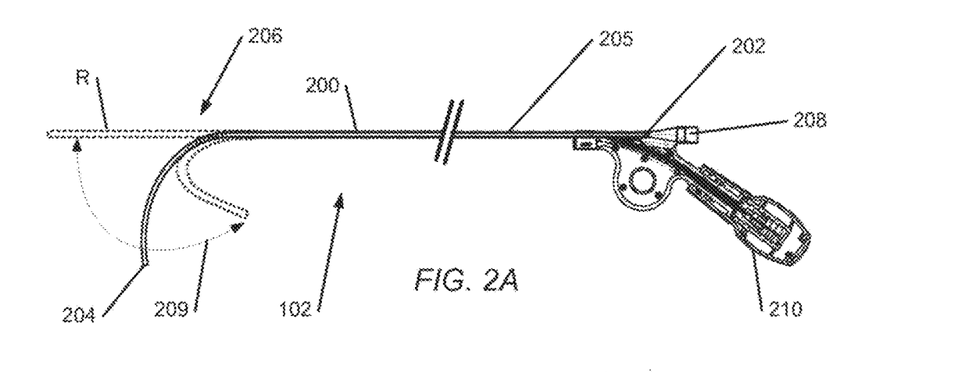
FIG. 2A is a side cross-sectional view of a deflectable catheter in accordance with an embodiment of the invention.

FIG. 2A is a side cross-sectional view of the deflectable catheter 102 in accordance with an embodiment of the invention. In general, the deflectable catheter 102 includes an elongate tubular member 200 that defines a lumen extending between a proximal end 202 and a distal end 204 of the tubular member 200. The lumen is adapted to telescopically receive the lead delivery catheter 104 shown in FIG. 1. The tubular member also has a generally straight portion 205 and an adjustable portion 206 adjacent to the distal end 204 of the member. The catheter 102 includes a hub 208 at the proximal end of the tubular member and an adjustable catheter handle 210 that can be manipulated, e.g., rotated, to deflect the adjustable portion 206 of the catheter. The catheter 102 can be manufactured from any suitable biocompatible material. In some cases it is made from polyether block amide.

The adjustable portion 206 can be provided with one of a variety of curved configurations in its relaxed and/or deflected state. As shown in FIG. 2A, in an initial relaxed state R, the adjustable portion 206 is a substantially straight continuation of the generally straight portion 205. The adjustable portion 206 can then be moved through a range of deflection 209 by turning the handle 210. In an alternative embodiment, the adjustable portion 206 may be provided with a resilient, flexible curve in its initial relaxed state that can also be deflected. Turning to FIG. 2C, in some cases the adjustable portion 206 may deflect back toward the catheter hub by an angle 207 of at least 135 degrees. The deflection can be used to align the outlet at the distal end 204 of the tubular member to i) guide a puncturing tool toward the atrial septum for creating a septal puncture, and/or ii) guide insertion of a second tubular member (i.e., delivery catheter 104) through the septal puncture into a left atrium of the heart. Thus, a single deflectable outer catheter can be designed, manufactured, and used without the need for multiple outer catheters of varying shapes.

Although not shown in the figures, according to some embodiments the adjustable portion 206 (and optionally part of the straight portion 205) is provided with an out-of-plane or three-dimensional configuration. Referring to FIG. 2A, the handle 210 and the straight portion 205 of the tubular member can define a reference plane. While is some cases the adjustable portion 206 remains within the reference plane (thus providing a two-dimensional range of deflection), in at least one configuration the distal end 204 of the adjustable portion 206 extends in to or out from the reference plane. For example, the adjustable portion 206 may be preformed with a resilient curve such that the distal end 204 extends transversely out from or in to the reference plane by an amount ranging from 0-90 degrees. In some cases the out-of-plane angle may range between 45-90 degrees. Thus, as the adjustable portion 206 is swept through the range of deflection, the distal end of the catheter moves outside the reference plane.

In another configuration, the adjustable portion 206 is within the reference plane in a relaxed state, but can be deflected back toward the handle 210 along a three-dimensional path within the reference plane or out from the reference plane. In this case the range of deflection is not solely a planar range, but can include a volumetric or three-dimensional range such as a portion of a sphere. In some cases the range of deflection may extend out from the reference plane between 0-90 degrees or between 45-90 degrees in either direction. Thus, the adjustable or deflectable portion 206 of the catheter 102 advantageously lets the catheter accommodate or compensate for variations in anatomy across classes of patients.

Figure 2B:
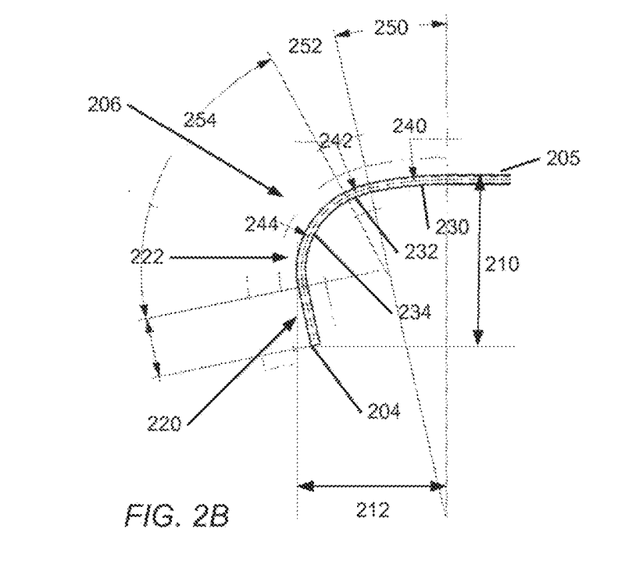
FIGS. 2B and 2C are partial cross-sectional views of the deflectable catheter of FIG. 2A.
Figure 2C:
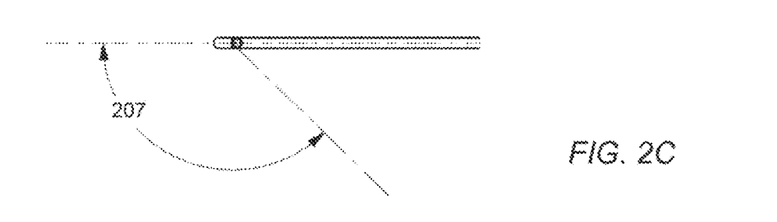

FIG. 2B is a partial cross-sectional view illustrating the adjustable portion 206 of the deflectable catheter 102 in one possible deflection state. In some embodiments the deflectable catheter 102 is adapted for being inserted into the right atrium through the superior vena cava and then deflected to approach the intra-atrial septum. In one case the catheter 102 is provided with an inner diameter to accommodate passage of multiple catheters and/or instruments therethrough, while also being equipped with a curved section dimensioned to accommodate the typical anatomy of the superior vasculature, the right atria, and the intra-atrial septum. For example, according to some embodiments the first tubular member 200 has an inner diameter between about 0.08-0.12 inches, between about 0.9-0.11 inches, or of about 0.1 inch. In some embodiments, the adjustable portion 206 of the catheter 102 may have a reach 210 of between about 2-3 inches, between about 2.1-2.8 inches, or about 2.4 inches in a deflected state. In some cases the adjustable portion 206 of the deflectable catheter 102 has a longitudinal length 212 of between about 0-4 inches, between about 1-3 inches, or of about 2 inches or about 2.12 inches in one preferred deflection state.

Continuing with reference to FIG. 2B, in one preferred deflection state, the first tubular member's adjustable portion 206 includes a short, straight portion 220 (e.g., about 0.85 inches long in some cases) adjacent the distal end 204 and a curved portion 222 connected between the straight portion 220 and the generally straight portion 205. In some cases the curved portion 222 comprises multiple curved segments forming a compound curve. Referring to FIG. 2B, in some cases the curved portion 222 has a first curved segment 230 connected to the generally straight portion 205, a second curved segment 232 connected to the first curved segment 230 and a third curved segment 234 connected to the second curved segment 232.

According to an embodiment of the invention, each of the multiple curved segments has a different radius of curvature designed to adapt the adjustable portion 206 for use within the right atrium. For example, in some cases the first curved segment 230 has a radius of curvature 240 between about 3 and about 4 times greater than the radii of curvature 242, 244 of the second and the third curved segments, respectively. In a specific example, the radius of curvature 240 of the first curved segment is about 4.86 inches, the radius of curvature 242 of the second curved segment is about 1.36 inches, and the radius of curvature 244 of the third curved segment is about 1.17 inches.

According to another embodiment of the invention, each of the multiple curved segments has a different subtended angle designed to adapt the adjustable portion 206 for use within the right atrium. For example, in some cases the third curved segment 234 has a subtended angle 254 between about 3 and about 7 times greater than the subtended angles 250, 252 of the first and the second curved segments, respectively. In one embodiment the first subtended angle 250 and the second subtended angle 252 are each between about 10 degrees and about 20 degrees, while the third subtended angle 254 is between about 60 degrees and about 90 degrees. In another embodiment the first subtended angle 250 is between about 12 and 13 degrees, the second subtended angle 252 is between about 14 and about 16 degrees, and the third subtended angle 254 is between about 70 and 80 degrees. Still more specifically, in one embodiment the first subtended angle 250 is about 12.7 degrees, the second subtended angle 252 is about 15 degrees, and the third subtended angle 254 is about 74.2 degrees.

Of course these are just a few examples of particular designs for one deflection state of a deflectable catheter according to embodiments of the invention. Other possible designs for an outer catheter not shown here include an out-of-plane design (as opposed to the two-dimensional design illustrated in the figures), the use of a fixed-shape catheter instead of an adjustable catheter, and/or a catheter designed for intra-atrial access from the inferior vena cava. In the case of the latter, the curved portion of the catheter would have a generally more open angle to accommodate the particular anatomy encountered when advancing through the inferior vena cava.

Figure 3A:
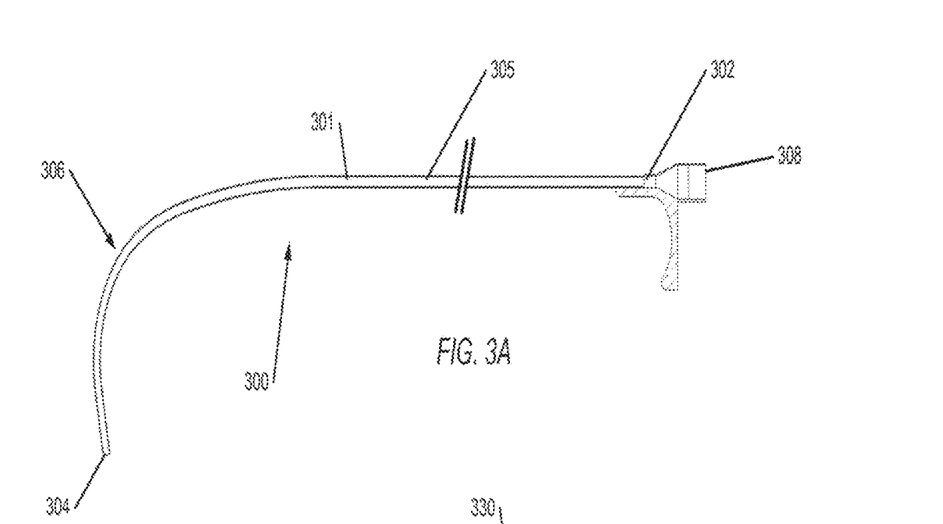
FIG. 3A is a side cross-sectional view of a lead delivery catheter in accordance with an embodiment of the invention.

FIG. 3A is a side cross-sectional view of a lead delivery catheter 300 in accordance with an embodiment of the invention. The lead delivery catheter 300 generally includes an elongated second tubular member 301 defining a lumen extending between a proximal end 302 and a distal end 304 of the second tubular member 301. A hub 308 is coupled to the lumen at the proximal end 302 of the tubular member 301. In some embodiments the lumen is adapted to receive one or more of the puncturing tool 108, the dilator 106, and/or an instrument to be placed in the heart, such as an electrical lead. The second tubular member 301 also includes a generally straight portion 305 and, in a relaxed state, a curved portion 306 adjacent its distal end 304.

The curved portion 306 of the delivery catheter 300 is a resilient, flexible curve in the catheter body, the type of which are well known in the art. Accordingly, the curved portion 306 straightens as the delivery catheter 300 is tracked over the dilator 106, but reverts back to its normally relaxed, curved shape when the dilator 106 is removed. According to an embodiment of the invention, the delivery system 100 utilizes the resiliency of the curved portion 306 to steer the delivery system 100 without use of the deflectable catheter. For example, in some cases the deflectable catheter is advanced up to the intra-atrial septal wall, but not advanced through the septal puncture. The lead delivery catheter is tracked over the dilator 106 and a guide wire/transseptal wire into the left atrium. To reach the left ventricle, at this point the dilator 106 is withdrawn and the delivery catheter resumes its normally curved shape, thus directing the guide wire toward the mitral valve and into the left ventricle. Once stationed within the left ventricle, the guide wire can be used to track the delivery catheter into the left ventricle while the deflectable catheter remains in the right atrium. After removing the guide wire, the lead delivery catheter provides a passage for advancing an instrument (e.g., electrical lead) into the left ventricle.

Figure 3B:
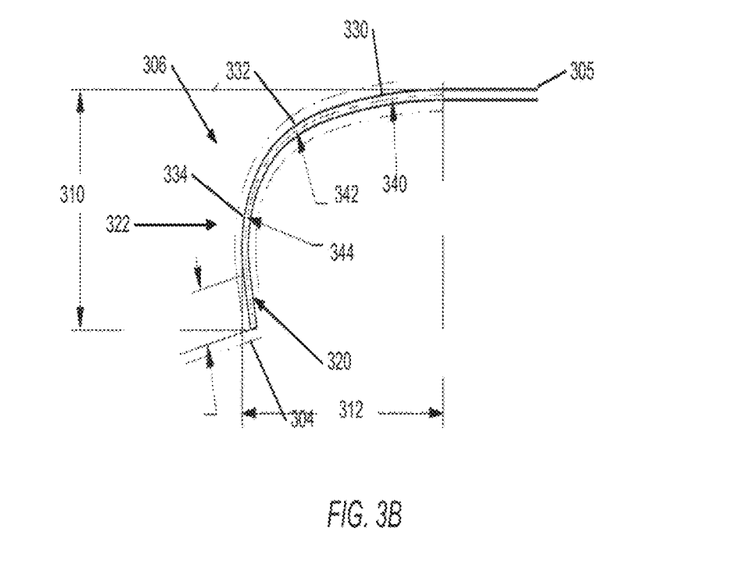
FIG. 3B is a partial cross-sectional view of the lead delivery catheter of FIG. 3A.

According to some embodiments, the second tubular member's curved portion 306 includes a short, straight portion 320 (e.g., about 0.498 inches long in some cases) adjacent the distal end 304 and a curved portion 322 connected between the straight portion 320 and the generally straight portion 305. In some cases the curved portion 322 comprises multiple curved segments forming a compound curve. Referring to FIG. 3B, in some cases the curved portion 322 has a first curved segment 330 connected to the generally straight portion 305, a second curved segment 332 connected to the first curved segment 330 and a third curved segment 334 connected to the second curved segment 332.

According to an embodiment of the invention, each of the multiple curved segments has a different radius of curvature designed to adapt the curved portion 306 for use within the left atrium. For example, in some cases the first curved segment 330 has a radius of curvature 340 between about 7 inches and about 9 inches, the radius of curvature 342 of the second curved segment 332 is between about 2 inches and about 3 inches, and the radius of curvature 344 of the third curved segment 334 is between about 1 inch and about 2 inches. In a specific example, the radius of curvature 340 of the first curved segment is about 7.96 inches, the radius of curvature 342 of the second curved segment is about 2.230 inches, and the radius of curvature 344 of the third curved segment is about 0.100 inches.

In some embodiments the curved portion 306 of the catheter 300 may have a relaxed reach 310 of between about 1-3 inches, between about 1.5-2.5 inches, or about 2.1 inches. In some cases the curved portion 306 of the delivery catheter 300 has a longitudinal length 312 of between about 1-5 inches, between about 2-4 inches, or of about 2.931 inches.

Upon advancing into the left ventricle, the curved portion 306 of the delivery catheter 300 can be useful for placing a lead or other item at one of a plurality of locations upon the LV endocardial wall. In a typical operation, the delivery catheter 300 is rotatable within the deflectable catheter through an angular range of motion that in some cases is at least about 360 degrees. Thus, use of the deflectable catheter as a support or workstation for the delivery catheter to rotate in, as well as the curved portion of the delivery catheter, allow for lead placement at a variety of locations on the LV wall.

Referring again to FIGS. 3A and 3B, the somewhat open curve in this example can be useful for placing a lead or other instrument near the left ventricular apex.

Figure 4A:
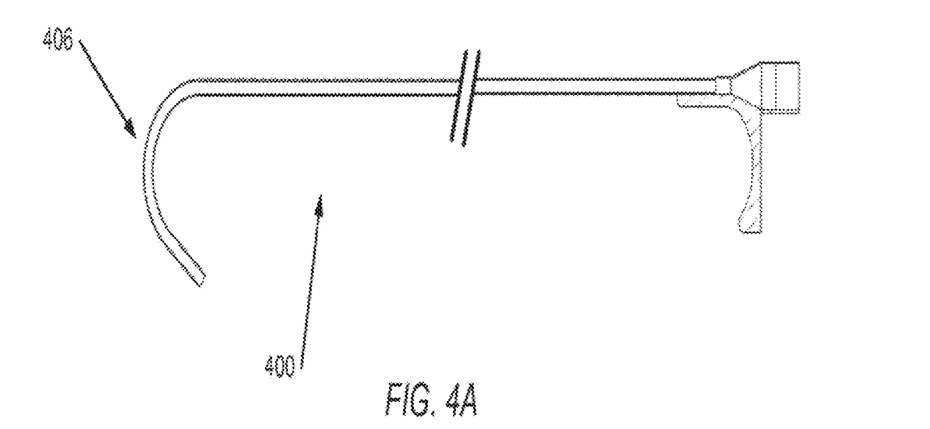
FIG. 4A is a side cross-sectional view of a lead delivery catheter in accordance with an embodiment of the invention.
Figure 4B:
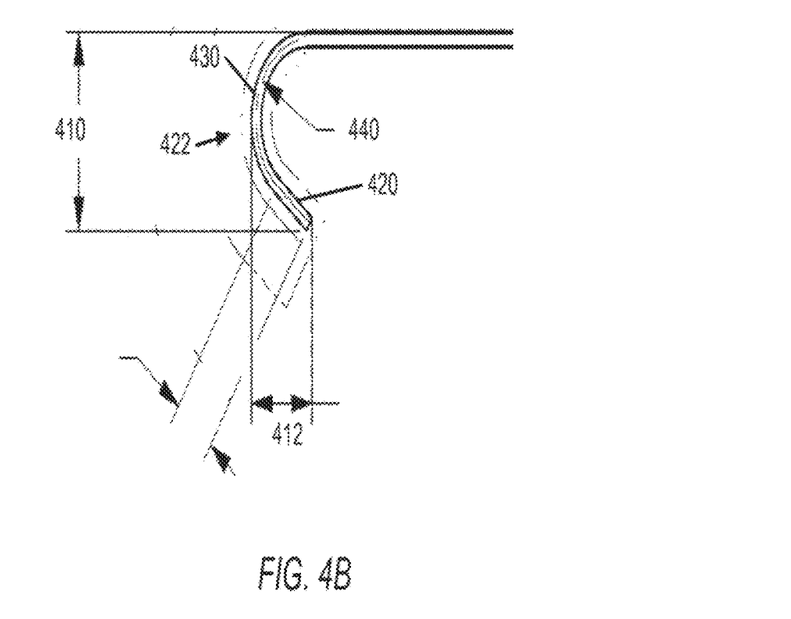
FIG. 4B is a partial cross-sectional view of the lead delivery catheter of FIG. 4A.

FIGS. 4A and 4B illustrate another example of a delivery catheter 400 that can be useful for placing a lead underneath the cusp of the mitral valve. The delivery catheter 400 is similar in many respects to the catheter shown in FIGS. 3A-3B, and thus is only briefly described. Of particular note is that the delivery catheter 400 includes a curved portion 406 that includes a straight portion 420 (e.g., about 0.394 inches long in some cases) and a curved portion 422 that comprises a single curved segment 430. In some cases the curved segment 430 has a radius of curvature 440 of between about 0 and about 1 inch, and in some cases about 0.5 inches. In some embodiments the curved portion 406 of the catheter 400 may have a relaxed reach 410 of between about 0.5-1.5 inches or about 1.184 inches. In some cases the curved portion 406 of the delivery catheter 400 has a longitudinal length 412 of about 0.590 inches.

Figure 5A:
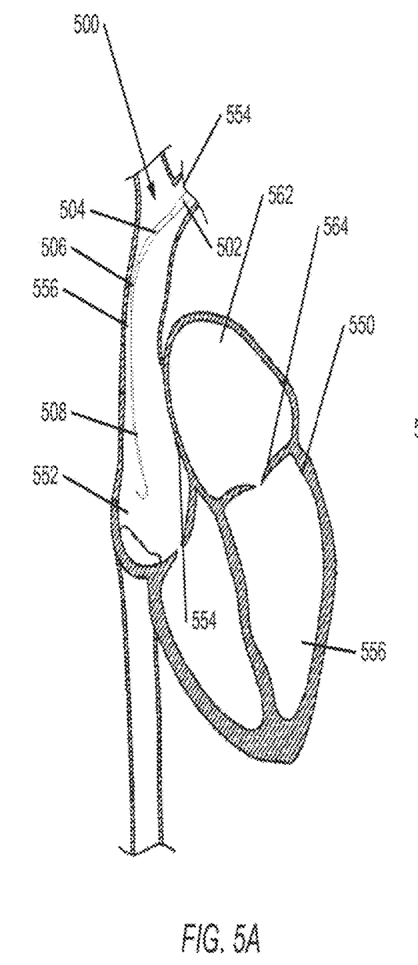
FIGS. 5A-5F are cross-sectional views illustrating a sequence of steps for accessing a left ventricle in accordance with an embodiment of the invention.

FIGS. 5A-5F are cross-sectional views illustrating a sequence of steps for accessing a left ventricle in accordance with an embodiment of the invention. Referring first to FIG. 5A, in this embodiment a catheter delivery system 500, similar to the embodiments described herein above, is advanced into the right atrium 552 of the heart 550 via the left subclavian vein 554 and the superior vena cava 556. The catheter delivery system 500 generally includes an elongate first tubular member 502 including an adjustable portion adjacent its distal end of the same character as the deflectable catheters described above. The system 500 further includes a second tubular member 504 including a normally curved portion 505 adjacent its distal end that straightens when advanced through the first tubular member 502 and over a stiffening member 506 (e.g., a dilator). The system 500 also includes a transseptal puncturing tool 508, such as a transseptal RF wire.

Figure 5B:
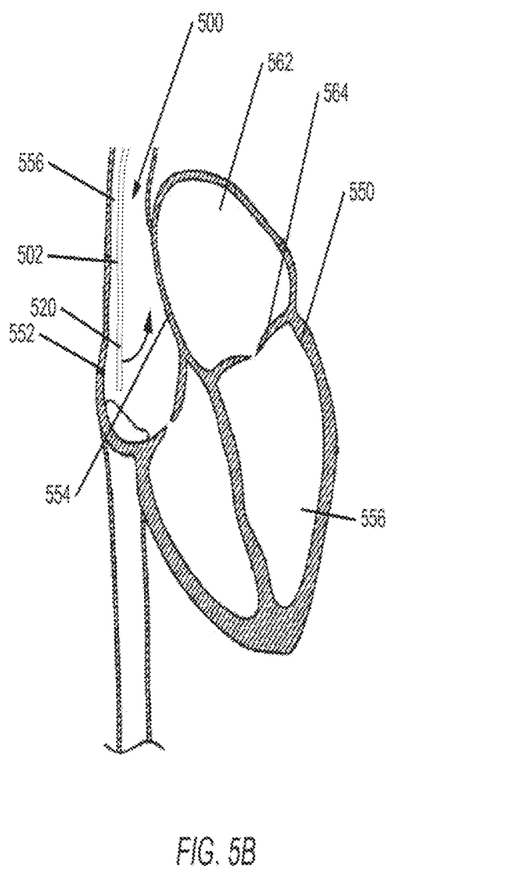
Figure 5C:
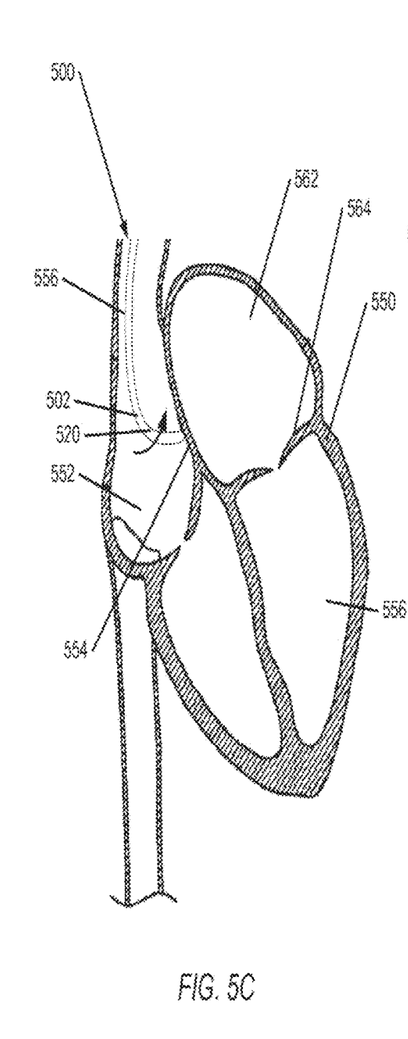

Continuing with reference to FIG. 5A, the method includes advancing the transseptal puncturing tool 508 (or alternatively a simple guide wire) into the right atrium 552, and then tracking the dilator 506, the second tubular member 504, and the first tubular member 502 over the guide 508 through the superior vena cava 556 into the right atrium 552 of the heart 550. Referring to FIGS. 5B and 5C, the method further includes deflecting an adjustable portion 520 of the first tubular member within the right atrium 552 toward the atrial septum 560 of the heart 550. In some embodiments the method optionally includes tenting the atrial septum 560 at or near the fossa ovalis with the second tubular member 504 and/or the dilator 506, and puncturing the atrial septum 560 with the puncturing tool 508. For example, a transseptal RF wire (e.g., Baylis Medical RF wire) can be energized (e.g., 25 W for 2 seconds) to form a small puncture hole in the septum. In some cases, though, an atrial puncture may already be present (from previous puncture, or naturally) and a separate puncture tool is not necessary.

Figure 5D:
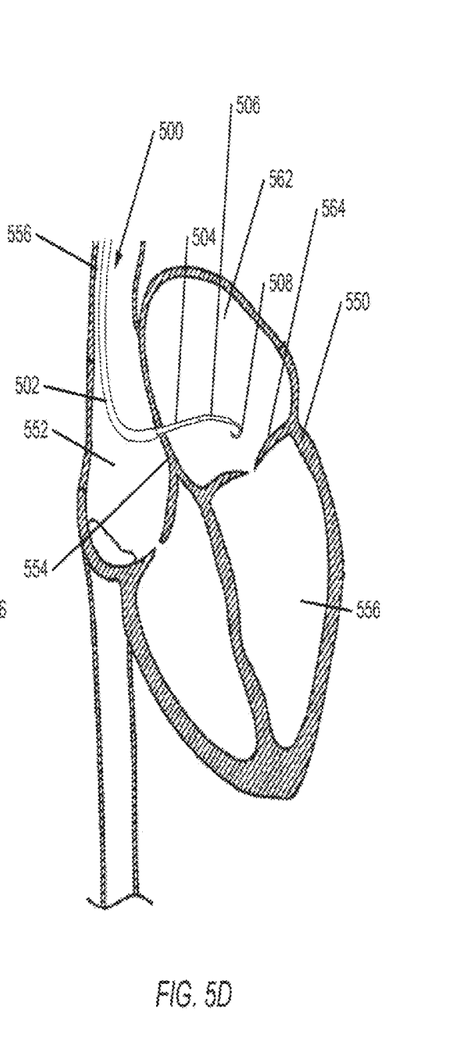
Figure 6A:
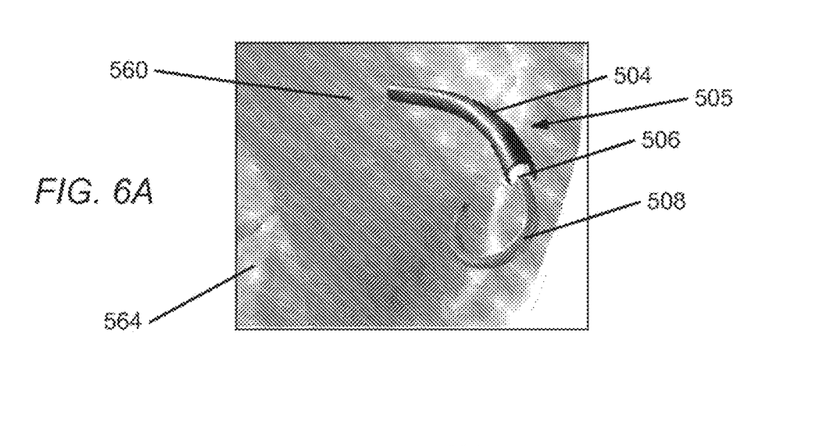
FIGS. 6A-6B are perspective views of a curved portion of a lead delivery catheter within a left atrium in accordance with an embodiment of the invention.
Figure 6B:
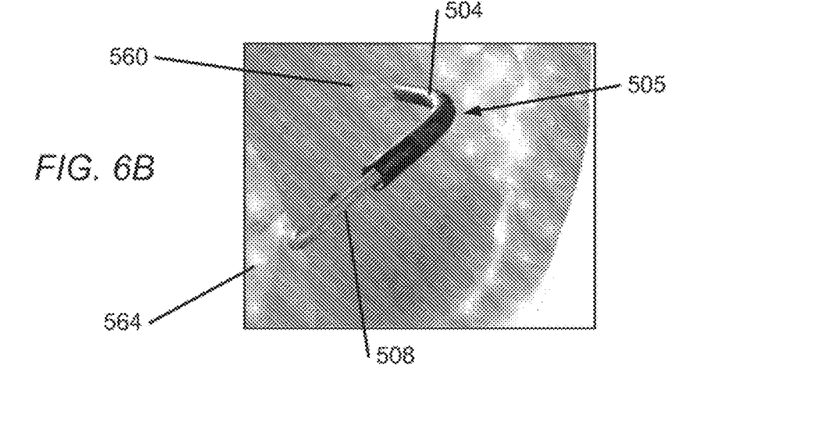

Turning to FIG. 5D, the method includes advancing the guide wire or puncturing tool 508 through the atrial septum 560 into the left atrium 562. The stiffening member or dilator 506 and the second tubular member 504 are then tracked over the guide 508 into the left atrium 562, while maintaining the first tubular member in the right atrium 552. At this point, the method includes withdrawing the stiffening member 506 from at least a portion of the second tubular member 504, thereby allowing the curved portion 505 to regain its normally curved shape. Upon regaining its curved shape, the outlet at the distal end of the second tubular member 504 is directed toward the mitral valve 564 and the left ventricle 566 of the heart 550. In some cases slight adjustment may be desirable, and the distal end of the second tubular member 504 can be rotated within the first tubular member 502 to more directly align it with the mitral valve 564. FIGS. 6A and 6B provide perspective views of before and after withdrawing the dilator 506 to allow the second tubular member 504 to regain its resting state curve 505

Figure 5E:
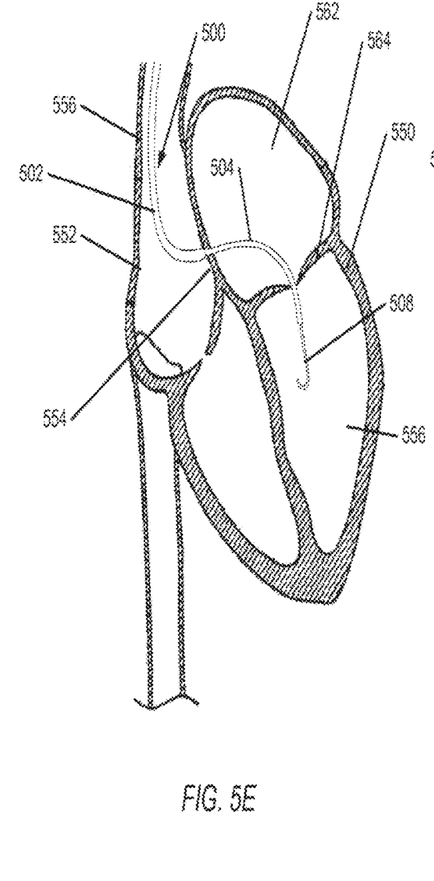
Figure 5F:
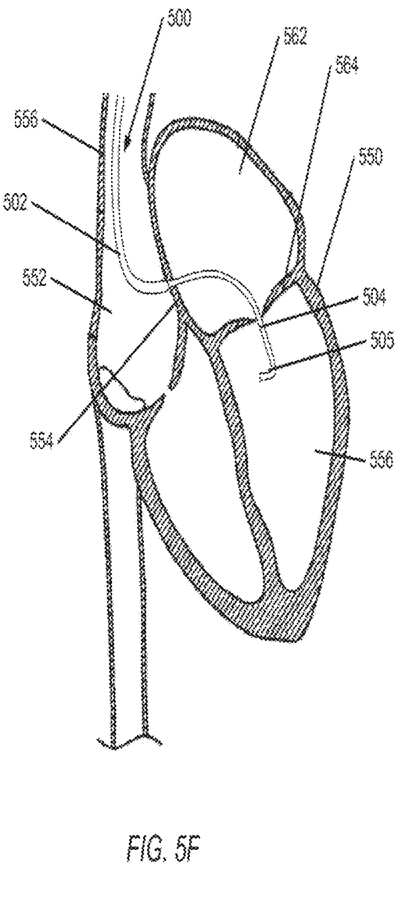
Figure 7:
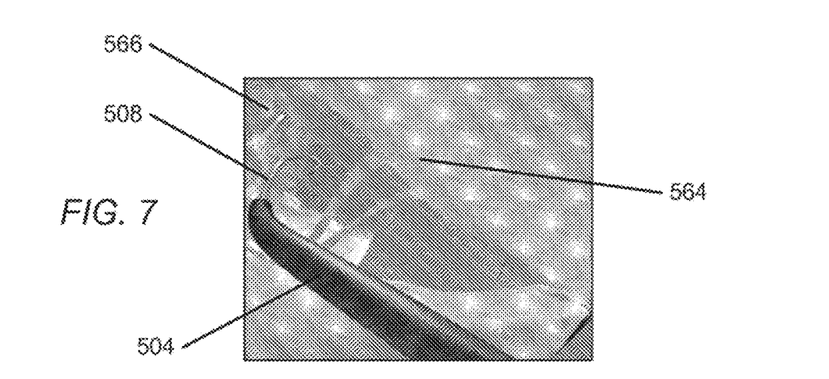
FIG. 7 is a perspective view of a guide wire and lead delivery catheter advanced through a mitral valve into a left ventricle in accordance with an embodiment of the invention.

Turning to FIGS. 5E and 7, after aligning the second tubular member with the mitral valve 564, the method includes advancing the guide 508 through the second tubular member 504 into the left ventricle 566. Referring to FIGS. 5E, 5F, and 7, the second tubular member 504 is then tracked over the guide 508 into the left ventricle 566, while the first tubular member 502 is still maintained in the right atrium 552.

Figure 8A:
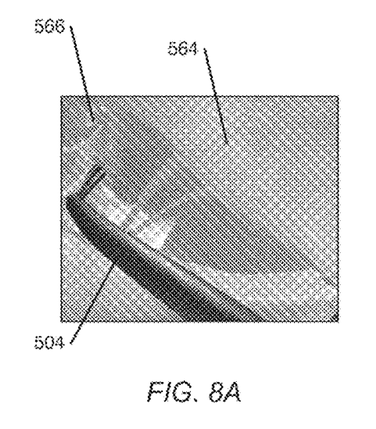
FIGS. 8A-8C are perspective views illustrating multiple rotational positions of a lead delivery catheter within a left ventricle in accordance with an embodiment of the invention.
Figure 8B:
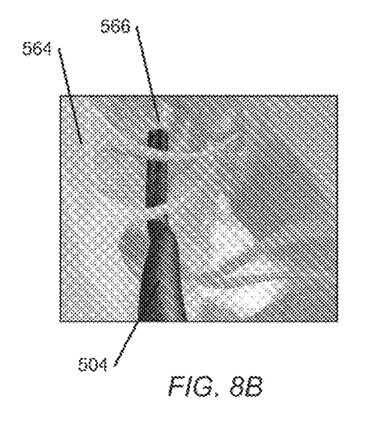
Figure 8C:
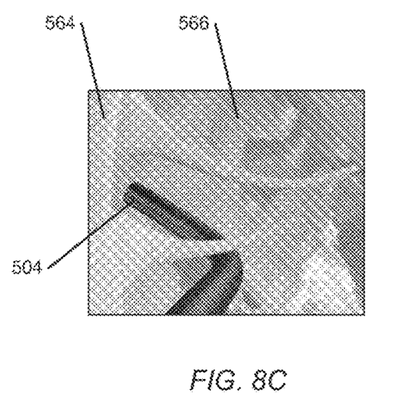
Figure 9:
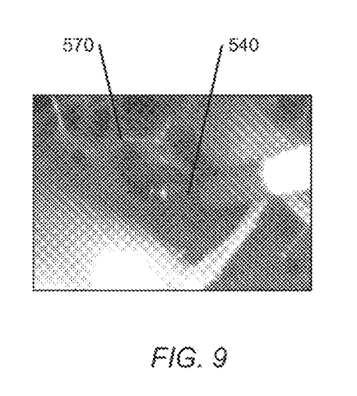
FIG. 9 is a perspective view illustrating placement of an electrical lead within a left ventricle in accordance with an embodiment of the invention.

Thus, the catheter delivery system 500 can provide a passage from exterior the patient into the left ventricle 566 for placing an instrument, such as a lead. FIGS. 8A-8C illustrate the second tubular member having resumed its natural curved state, thus providing an advantageous angled distal tip for sweeping about the left ventricle 566 as the second tubular member 504 is rotated within the first tubular member 502. Accordingly, an instrument, such as the lead 540 shown in FIG. 8, can be placed at any one of a plurality of locations on the endocardial wall 570 of the left ventricle 566.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. A method of transseptal delivery of an instrument into a heart, comprising:
   employing an elongate first tubular member defining a first lumen extending between a proximal end and a distal end of the first tubular member, the first tubular member having an adjustable portion adjacent its distal end and an elongate second tubular member received within the first tubular member, the second tubular member defining a second lumen extending between a proximal end and a distal end of the second tubular member, the second lumen adapted to receive a puncturing tool and an instrument to be placed in the heart, the second tubular member having a curved portion adjacent its distal end in a relaxed state; by:
   a) advancing the first tubular member such that it extends through a superior entry point into a right atrium of the heart;
   b) deflecting the adjustable portion of the first tubular member toward an atrial septum of the heart;
   c) guiding the puncturing tool through the second tubular member and creating a septal puncture;
   d) inserting the second tubular member through the septal puncture into a left atrium of the heart;
   e) with the first tubular member remaining in the right atrium and with the second tubular member extending through the septal puncture into the left atrium, orienting the curved portion of the second tubular member toward a left ventricle of the heart;
   f) advancing a guide through the second tubular member into the left ventricle;
   g) with the first tubular member remaining in the right atrium, advancing the second tubular member along the guide into the left ventricle; and
   h) with the first tubular member remaining in the right atrium and the second tubular member extending into the left ventricle, advancing the instrument into the left ventricle.

2. The delivery method of claim 1, wherein the second tubular member is rotatable within the first tubular member through an angular range of motion.

3. The delivery method of claim 2, wherein the angular range of motion is at least 360 degrees.

4. The delivery method of claim 1, further comprising inserting dilator within the second tubular member prior to advancement of the second tubular member through the septal puncture.

5. The delivery method of claim 1, wherein the puncturing tool is an RF puncture tool or a mechanical puncture tool.

6. The delivery method of claim 1, wherein the instrument is an electrical lead.

7. The delivery method of claim 1, wherein the first tubular member includes an elongated generally straight portion connected to the adjustable portion, wherein deflecting the adjustable portion comprises causing the curved portion to assume a configuration comprising a first curved segment connected to the generally straight portion, a second curved segment connected to the first curved segment and a third curved segment connected to the second curved segment, each curved segment having a different radius of curvature.

8. The delivery method of claim 7, wherein, in the configuration, the first curved segment has a radius of curvature between about 3 and about 4 times greater than the radii of curvature of the second and the third curved segments.

9. The delivery method of claim 7, wherein, in the configuration, the third curved segment has a subtended angle between about 3 and about 7 times greater than subtended angles of the first and the second curved segments.

10. The delivery method of claim 7, wherein, in the configuration, the first and the second curved segments have subtended angles between about 10 degrees and about 20 degrees and the third curved segment has a subtended angle between about 60 degrees and about 90 degrees.

11. The delivery method of claim 7, wherein' in the configuration, the first curved segment has a subtended angle of between about 12 degrees and about 13 degrees, the second curved segment has a subtended angle of between about 14 degrees and 16 degrees, and the third curved segment has a subtended angle between about 70 degrees and about 80 degrees.

12. The delivery method of claim 1, wherein the adjustable portion of the first tubular member has a deflection angle of at least about 135 degrees with respect to a line extending from the generally straight portion.

13. The delivery method of claim 1, wherein the adjustable portion of the first tubular member is adjustable through a two-dimensional range of deflection.

14. The delivery method of claim 1, wherein the adjustable portion of the first tubular member is adjustable through a three-dimensional range of deflection.

15. The delivery method of claim 1, wherein the adjustable portion of the first tubular member is curved in a relaxed state.

16. The delivery method of claim 15, wherein the curve of the adjustable portion of the first tubular in the relaxed state portion comprises an out-of-plane configuration.

17. The delivery method of claim 1, wherein in a relaxed state the curved portion of the second tubular member has a first curved segment connected to a generally straight portion of the tubular member, a second curved segment connected to the first curved segment and a third curved segment connected to the second curved segment, each curved segment having a different radius of curvature, wherein the radius of curvature of the first curved segment is between about 7 inches and about 9 inches, the radius of curvature of the second curved segment is between about 2 inches and about 3 inches, and the radius of curvature of the third curved segment is between about 1 inch and about 2 inches.

* * * * *